United States Patent
Seto et al.

(10) Patent No.: US 7,336,758 B2
(45) Date of Patent: Feb. 26, 2008

(54) RADIOGRAPHY SYSTEM

(75) Inventors: Masaru Seto, Tokyo (JP); Yasushi Sato, Tokyo (JP)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 51 days.

(21) Appl. No.: 11/295,242

(22) Filed: Dec. 5, 2005

(65) Prior Publication Data

US 2006/0120505 A1 Jun. 8, 2006

(30) Foreign Application Priority Data

Dec. 7, 2004 (JP) ............... 2004-354118

(51) Int. Cl.
*H05G 1/00* (2006.01)
*H05G 1/28* (2006.01)

(52) U.S. Cl. ............... 378/4; 378/162; 378/165

(58) Field of Classification Search ............ 378/4, 378/11, 19, 21, 62, 64, 65, 132–165

See application file for complete search history.

(56) References Cited

U.S. PATENT DOCUMENTS

| | | | |
|---|---|---|---|
| 5,531,520 A | | 7/1996 | Grimson et al. |
| 5,608,849 A | | 3/1997 | King, Jr. |
| 6,490,337 B1 | * | 12/2002 | Nagaoka et al. ............ 378/20 |
| 6,669,635 B2 | | 12/2003 | Kessman et al. |
| 6,795,521 B2 | * | 9/2004 | Hsu et al. ............ 378/4 |
| 6,920,347 B2 | | 7/2005 | Simon et al. |
| 6,947,584 B1 | | 9/2005 | Avila et al. |
| 6,947,786 B2 | | 9/2005 | Simon et al. |
| 6,968,224 B2 | | 11/2005 | Kessman et al. |
| 2004/0171924 A1 | * | 9/2004 | Mire et al. ............ 600/407 |

FOREIGN PATENT DOCUMENTS

| | | |
|---|---|---|
| JP | 2001-276056 | 10/2001 |
| JP | 2001-299741 | 10/2001 |
| JP | 2001-299742 | 10/2001 |

* cited by examiner

*Primary Examiner*—Edward J. Glick
*Assistant Examiner*—Irakli Kiknadze
(74) *Attorney, Agent, or Firm*—Armstrong Teasdale LLP

(57) ABSTRACT

A method to check a tissue located in the vicinity of an object of examination when a treatment instrument such as a puncture needle is inserted into a subject, wherein a first planar image construction block included in an image construction unit reconstructs in real time two-dimensional planar images, which represent subject's slice planes, on the basis of projection data. A stereoscopic image construction block included in the image construction unit constructs three-dimensional stereoscopic images, which represent the subject's slice planes, on the basis of projection data. The planar images constructed by the first planar image construction block are displayed in real time on the screen of a display unit, and the stereoscopic images constructed by the stereoscopic image construction block are displayed on the screen of the display unit while being juxtaposed with the first planar images constructed by the first planar image construction block.

11 Claims, 8 Drawing Sheets

RADIOGRAPHY SYSTEM

CROSS REFERENCE TO RELATED APPLICATIONS

This application claims the benefit of Japanese Application No. 2004-354118 filed Dec. 7, 2004.

BACKGROUND OF THE INVENTION

The present invention relates to a radiography system, or more particularly, to a radiography system that scans a subject with a radiation so as to acquire projection data, and reconstructs images of the subject using the acquired projection data.

Radiography systems including an X-ray computed tomography (CT) system reconstruct images of a subject's section on the basis of projection data acquired from the subject by scanning the subject, who lies down in a radiographic space, with a radiation.

The X-ray CT system is applied to diverse usages including medical use and industrial use, and used for, for example, fluoroscopy that is conducted using a treatment instrument such as a puncture needle. In the fluoroscopy, the X-ray CT system acquires in real time images of a subject's section and displays the images. An operator inserts the puncture needle to an object region of the subject, and checks the position of the puncture needle while looking at the images of the section displayed in real time in the X-ray CT system (refer to, for example, Patent Document 1, Patent Document 2, and Patent Document 3).

[Patent Document 1] Japanese Unexamined Patent Application Publication No. 2001-299742

[Patent Document 2] Japanese Unexamined Patent Application Publication No. 2001-299741

[Patent Document 3] Japanese Unexamined Patent Application Publication No. 2001-276056

To be more specific, in the foregoing fluoroscopy, first, a preliminary scan is performed on a region including an object of examination in a subject prior to a main scan intended to perform treatment using a puncture needle. Planar images that two-dimensionally represent a plurality of subject's axial planes are constructed. In other words, images representing a plurality of different slice planes that are lined longitudinally to the direction of the subject's body axis are constructed two-dimensionally. An operator uses the planar images constructed by performing the preliminary scan to determine the position of an object of examination. Thereafter, the X-ray CT system performs the main scan, and displays in real time the planar images of a section containing a region which covers the object of examination. Herein, the X-ray CT system displays the images of the plurality of different axial planes, that is, slice planes lined longitudinally to the subject's body axis. The operator references the planar images of the axial planes constructed by performing the preliminary scan and the planar images of the plurality of different axial planes displayed in real time during the main scan. Based on the planar images resulting from the preliminary scan, the puncture needle is inserted from a predetermined position. The operator observes the images of the sections displayed in real time and an image representing the needlepoint of the puncture needle. After the operator confirms that the puncture needle has reached the object of examination, the operator treats the subject using the puncture needle so as to achieve fluoroscopic diagnosis.

As mentioned above, in the fluoroscopy, the operator references the planar images of the axial planes, which result from the preliminary scan, and insert the puncture needle. Since the planar images are referenced, when the puncture needle is inserted, there is often difficulty in checking a tissue located in the vicinity of the object of examination. Therefore, in the conventional X-ray CT system, it is often hard to efficiently diagnose the object of examination.

SUMMARY OF THE INVENTION

An object of the present invention is to provide a radiography system capable of improving diagnostic efficiency.

In order to accomplish the above object, a radiography system in accordance with the present invention comprises: a scanner that scans a subject's scan field with a radiation so as to acquire projection data of the subject; an image construction unit that reconstructs in real time a first two-dimensional image of a slice plane of the subject; a display unit on the screen of which the first image constructed by the image construction unit is displayed in real time. The image construction unit constructs a second three-dimensional image of the subject's slice plane on the basis of the projection data. The first image and second image are displayed on the screen of the display unit while being juxtaposed to each other.

According to the present invention, there is provided a radiography system that contributes to improvement of diagnostic efficiency.

Further objects and advantages of the present invention will be apparent from the following description of the preferred embodiments of the invention as illustrated in the accompanying drawings.

BRIEF DESCRIPTION OF THE DRAWINGS

FIG. 7 includes diagrams showing a scene where treatment is performed using the puncture needle in combination with the embodiment of the present invention.

DETAILED DESCRIPTION OF THE INVENTION

An embodiment of the present invention will be described below.

Figure 1:
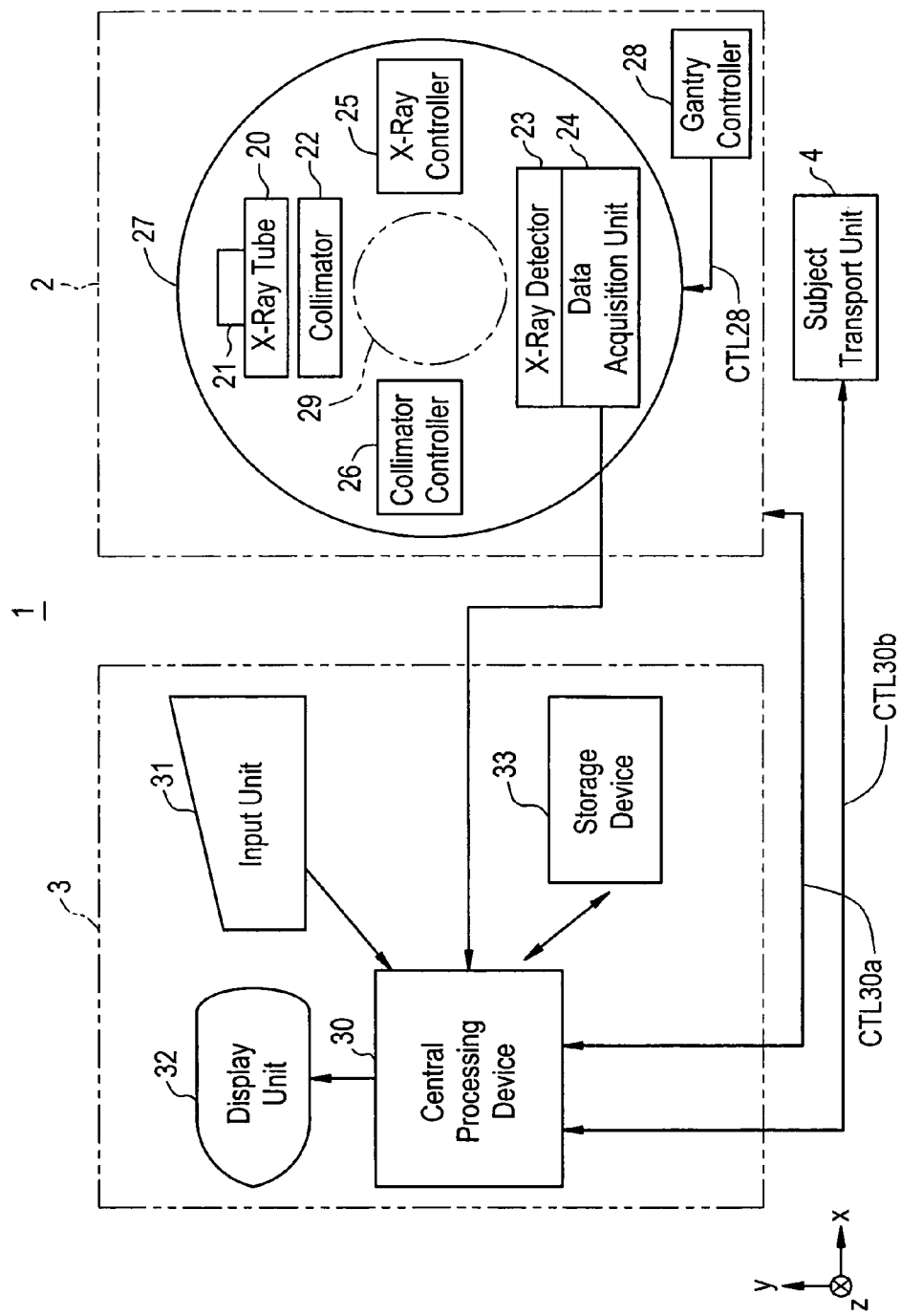
FIG. 1 is a block diagram showing the overall configuration of an X-ray CT system in accordance with an embodiment of the present invention.
Figure 2:
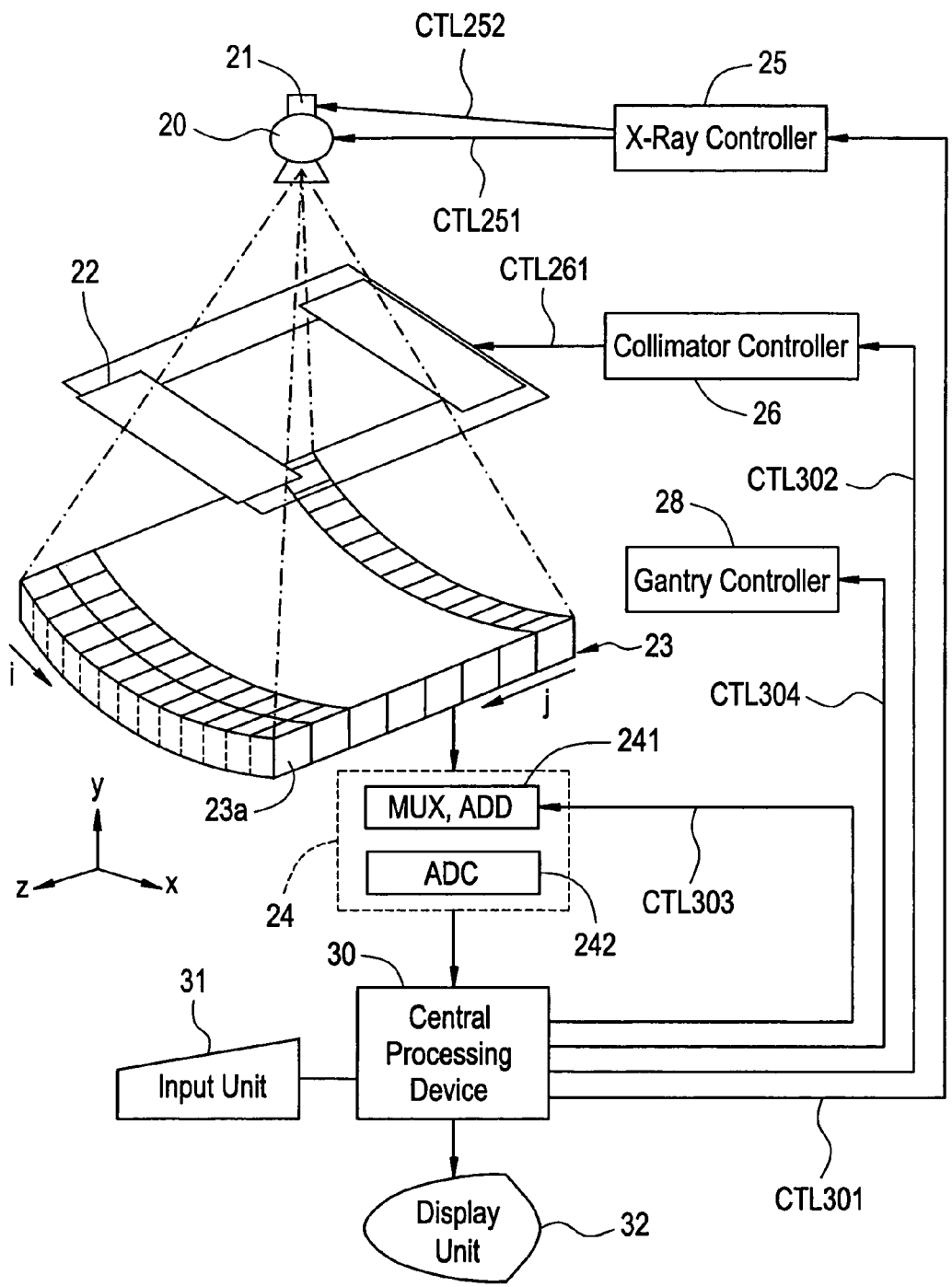
FIG. 2 shows the configuration of the major portion of the X-ray CT system in accordance with the embodiment of the present invention.

FIG. 1 is a block diagram showing the overall configuration of an X-ray CT system 1 in accordance with an embodiment of a radiography system of the present invention. FIG. 2 shows the configuration of the major portion of the X-ray CT system 1 in accordance with the embodiment.

As shown in FIG. 1, the X-ray CT system 1 comprises a scanner gantry 2, an operator console 3, and a subject transport unit 4.

The scanner gantry 2 scans a subject, which is moved by the subject transport unit 4 within a radiographic space 29, with X-rays according to a control signal CTL30a sent from the operator console 3, and acquires as raw data the projection data of the subject. The scanner gantry 2 comprises, as shown in FIG. 1, an X-ray tube 20, an X-ray tube mover 21, a collimator 22, an X-ray detector 23, a data acquisition unit 24, an X-ray controller 25, a collimator controller 26, a rotary housing 27, and a gantry controller 28.

Figure 3:
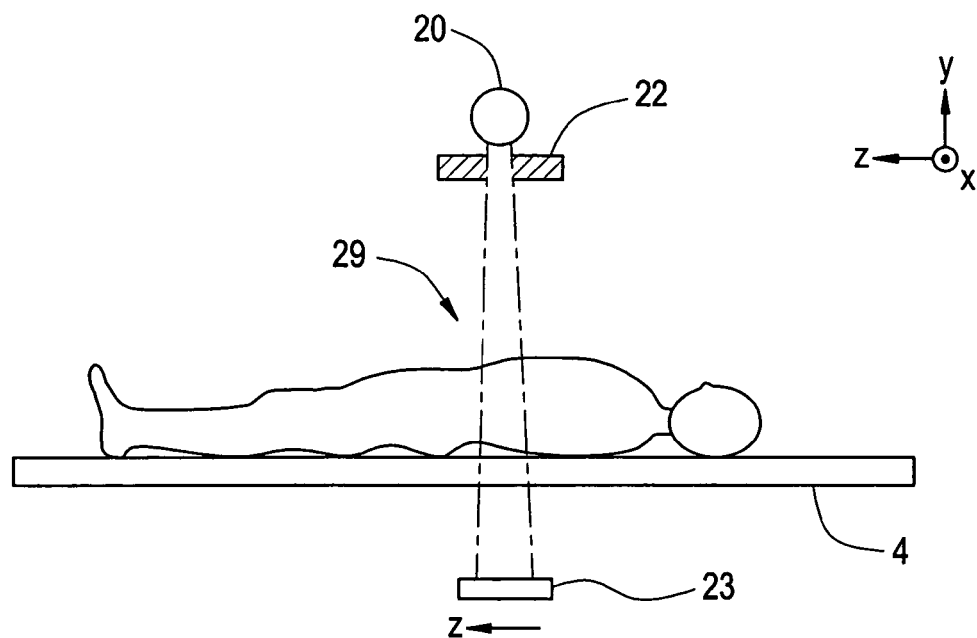
FIG. 3 shows the positional relationship among an X-ray tube, a collimator, and an X-ray detector which are included in a scanner gantry of the X-ray CT system in accordance with the embodiment of the present invention.

FIG. 3 shows the positional relationship among the X-ray tube 20, collimator 22, and X-ray detector 23 included in the scanner gantry 2.

As shown in FIG. 3, in the scanner gantry 2, the X-ray tube 20 and X-ray detector 23 are arranged with the radiographic space 29, into which a subject is carried, between them. The collimator 22 is disposed in order to recompose X-rays radiated from the X-ray tube 20. In the scanner gantry 2, the X-ray tube 20, collimator 22, and X-ray detector 23 are rotated about the subject with the direction z of the subject's body axis as an axis of rotation. Consequently, the X-ray tube 20 radiates X-rays in a plurality of directions of views about the subject, and the X-ray detector 23 detects X-rays radiated from the X-ray tube 20 and transmitted by the subject. Projection data is then produced. According to the present embodiment, the scanner gantry 2 performs a main scan intended to acquire first projection data as projection data by scanning a subject's scan field with X-rays. Furthermore, prior to the main scan, the scanner gantry 2 performs a preliminary scan, which is intended to acquire second projection data as projection data by scanning the subject's scan field with X-rays, in preparation for the main scan.

The components of the scanner gantry 2 will be described below.

The X-ray tube 20 is of, for example, a rotating anode type and irradiates X-rays to a subject. The X-ray tube 20 radiates, as shown in FIG. 2, X-rays of predetermined strength to the subject's scan field via the collimator 22 according to a control signal CTL251 sent from the X-ray controller 25. X-rays radiated from the X-ray tube 20 are recomposed into, for example, a conical beam by means of the collimator 22, and then irradiated toward the X-ray detector 23. The X-ray tube 20 is rotated about the subject by the rotary housing 27 with the direction z of the subject's body axis as an axis of rotation so that the X-rays will be irradiated to the subject in the directions of views around the subject. In other words, the X-ray tube 20 is rotated about the subject with an axis along a direction, in which the subject transport unit 4 moves the subject within the radiographic space 29, as a center of rotation.

The X-ray tube mover 21 shifts the center of radiation of the X-ray tube 20 according to a control signal CTL252 sent from the X-ray controller 25 so that the center of radiation will be aligned with the direction z of the subject's body axis within the radiographic space 29 of the scanner gantry 2.

The collimator 22 is, as shown in FIG. 2, interposed between the X-ray tube 20 and X-ray detector 23. The collimator 22 comprises, for example, two plates disposed in a direction i of channels and two plates disposed in a direction j of arrays. The collimator 22 moves the two pairs of plates disposed in the respective directions independently of each other according to a control signal CTL261 sent from the collimator controller 26. Thus, the collimator 22 intercepts X-rays radiated from the X-ray tube 20 in both the directions so as to recompose the X-rays into a conical beam, and thus adjusts an X-irradiation range.

The X-ray detector 23 detects X-rays radiated from the X-ray tube 20 and transmitted by a subject, and produces projection data of the subject. The X-ray detector 23 is rotated together with the X-ray tube 20 about the subject by means of the rotary housing 27. The X-ray detector 23 then detects the X-rays, which are radiated in different directions about the subject and transmitted by the subject, so as to produce projection data.

Moreover, the X-ray detector 23 comprises, as shown in FIG. 2, a plurality of detector elements 23a. The X-ray detector 23 has the detector elements 23a two-dimensionally set in array in the direction i of channels, which corresponds to a direction of rotation in which the X-ray tube 20 is rotated with the direction z of the subject's body axis as a center of rotation by means of the rotary housing 27, and the direction j of arrays corresponding to the direction of the axis of rotation serving as a center of rotation about which the X-ray tube 20 is rotated by the rotary housing 27. The X-ray detector 23 has a surface thereof curved in a cylindrical concave form because of the plurality of detector elements 23a that is two-dimensionally set in array.

The detector elements 23a constituting the X-ray detector 23 each include a scintillator (not shown) that converts detected X-rays into light, and a photodiode (not shown) that converts the light produced by the scintillator into charge. The X-ray detector 23 is designed as a solid-state detector. Incidentally, the configuration of the detector elements 23a is not limited to the above one. Alternatively, a semiconductor detector element that utilizes cadmium telluride (CdTe) or the like or an ion chamber-type detector element 23a that utilizes xenon gas will do.

The data acquisition unit 24 is included for acquiring projection data produced by the X-ray detector 23. The data acquisition unit 24 acquires projection data items produced by the respective detector elements 23a of the X-ray detector 23, and transfers them to the operator console 3. As shown in FIG. 2, the data acquisition unit 24 comprises a selection/addition switching circuit (MUX,ADD) 241 and an analog-to-digital converter (ADC) 242. The selection/addition switching circuit 241 selects any of projection data items sent from the detector elements 23a included in the X-ray detector 23 according to a control signal CTL303 sent from a central processing device 30, or summates projection data items by changing the set of projection data items and then transfers the result of the summation to the analog-to-digital converter 242. The analog-to-digital converter 242 converts projection data, which is selected by the selection/addition switching circuit 241 or results from summation of any set of projection data items, from an analog form to a digital form, and then transfers the resultant digital signal to the central processing device 30.

The X-ray controller 25 transmits, as shown in FIG. 2, a control signal CTL251 to the X-ray tube 20 in response to a control signal CTL301 sent from the central processing device 30, and thus controls X-irradiation. The X-ray controller 25 controls, for example, the tube current of the X-ray tube 20 or an irradiation time. Moreover, the X-ray controller 25 transmits a control signal CTL252 to the X-ray tube mover 221 in response to a control signal CTL301 sent from the central processing device 30, and thus controls the X-ray tube mover so that the center of radiation in the X-ray tube 20 will be aligned with the body-axis direction z.

The collimator controller 26 transmits, as shown in FIG. 2, a control signal CTL261 to the collimator 22 in response to a control signal CTL302 sent from the central processing device 30, and thus controls the collimator 22 so that the collimator 22 will recompose X-rays radiated from the X-ray tube 20.

The rotary housing 27 has, as shown in FIG. 1, a cylindrical shape and has the radiographic space 29 formed internally. The rotary housing 27 rotates about a subject with the direction z of the subject's body axis in the radiographic space 29 as a center of rotation according to a control signal CTL28 sent from the gantry controller 28. The rotary housing 27 accommodates the X-ray tube 20, X-ray tube mover 21, collimator 22, X-ray detector 23, data acquisition unit 24, X-ray controller 25, and collimator controller 26. The positional relationships between a subject carried into the radiographic space 29 and the components vary relative to a direction of rotation. Since the rotary housing 27 rotates, the X-ray tube 21 can irradiate X-rays to the subject in each of a plurality of directions of views around the subject. The X-ray detector 23 can detect X-rays, which are transmitted by the subject, in relation to each direction of a view. Moreover, the rotary housing 27 tilts according to a control signal CTL28 sent from the gantry controller 28. The rotary housing 27 tilts in the body-axis direction z with the iso-center in the radiographic space 29 as a fulcrum.

The gantry controller 28 transmits, as shown in FIG. 1 and FIG. 2, a control signal CTL28 to the rotary housing 27 in response to a control signal CTL304 sent from the central processing device 30 included in the operator console 3, and thus instructs the rotary housing 27 to rotate or tilt.

The operator console 3 will be described below.

The operator console 3 comprises, as shown in FIG. 1, the central processing device 30, an input unit 31, a display unit 32, and a storage device 33.

The central processing device 30 includes a computer and software installed in the computer, and performs various kinds of processing in response to a command an operator enters at the input unit 31.

Figure 4:
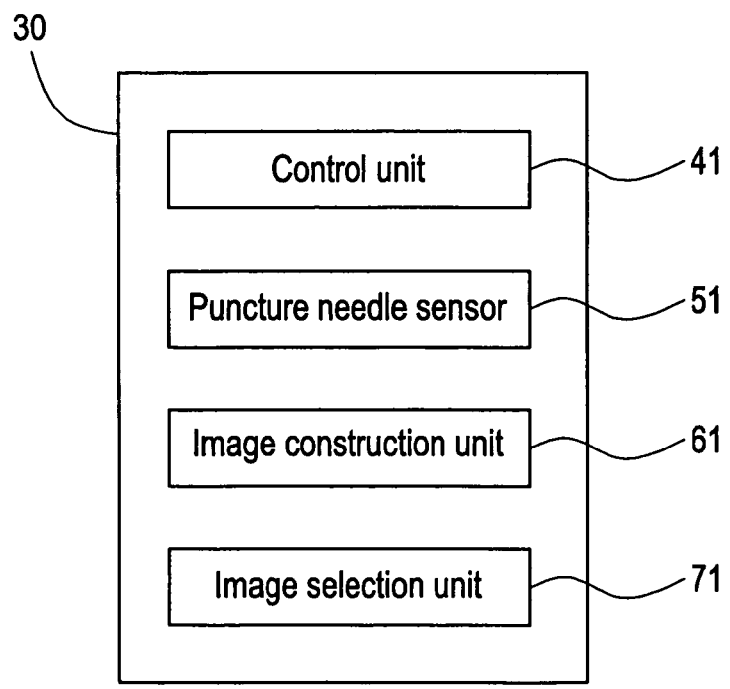
FIG. 4 is a functional block diagram showing the components of a central processing device included in the X-ray CT system in accordance with the embodiment of the present invention.

FIG. 4 is a functional block diagram showing the configuration of the central processing device 30.

As shown in FIG. 4, the central processing device 30 comprises a control unit 41, a puncture needle sensor 51, an image construction unit 61, and an image selection unit 71.

The control unit 41 is included for controlling the components of the X-ray CT system 1. For example, the control unit 41 receives the conditions for scanning an operator enters at the input unit 31, and transmits a control signal CTL30a to the components according to the conditions for scanning so as to execute a scan.

To be more specific, the control unit 41 transmits a control signal CTL30b to the subject transport unit 4, and thus instructs the subject transport unit 4 to carry a subject into the radiographic space 29. The control unit 41 then transmits a control signal CTL304 to the gantry controller 28, and thus causes the rotary housing 27 of the scanner gantry 2 to rotate. The control unit 41 then transmits a control signal CTL301 to the X-ray controller 25 so that X-rays will be radiated from the X-ray tube 20. The control unit 41 then transmits a control signal 302 to the collimator controller 26 and thus controls the collimator 22 so that the collimator 22 will recompose X-rays. Moreover, the control unit 42 transmits a control signal CTL303 to the data acquisition unit 24, and thus controls the data acquisition unit 24 so that the data acquisition unit 24 will acquire projection data items produced by the detector elements 23a of the X-ray detector 23.

When an operator uses a puncture needle to treat a subject's scan field during a main scan, the puncture needle sensor 51 senses the position in the subject of the puncture needle, with which the subject is treated, so as to produce puncture needle data. The puncture needle sensor 51 acquires a radio wave sent from the needlepoint of the puncture needle, and produces, as the puncture needle data, data items of the position and depth in the subject at which the needlepoint of the puncture needle is located, and data of the direction of the puncture needle. The puncture needle sensor 51 then transmits the produced puncture needle data to the image construction unit 61.

Based on projection data acquired by the data acquisition unit 24 included in the scanner gantry 2, the image construction unit 61 reconstructs images of a subject's section by performing arithmetic operations. Specifically, the image construction unit 61 performs pre-processing such as sensitivity correction or beam hardening on the projection data. Thereafter, the image construction unit 61 reconstructs images according to a filtering back projection technique so as to thus construct the images of a subject's section.

Figure 5:
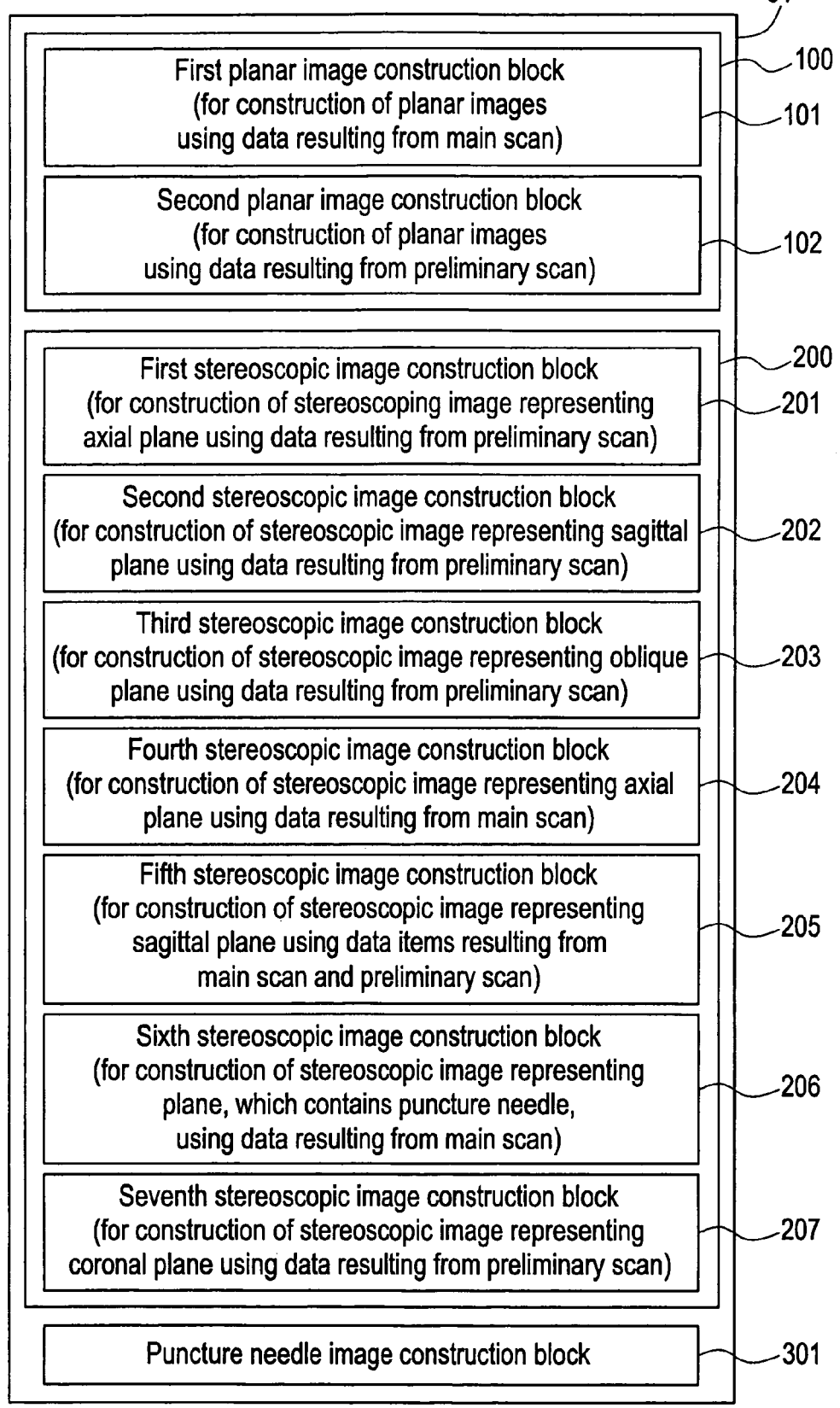
FIG. 5 is a functional block diagram showing the components of an image construction unit included in the X-ray CT system in accordance with the embodiment of the present invention.

FIG. 5 is a functional block diagram showing the configuration of the image construction unit 61.

As shown in FIG. 5, the image construction unit 61 comprises a planar image construction block 100, a stereoscopic image construction block 200, and a puncture needle image construction block 301. Based on projection data, the image construction unit 61 reconstructs a first planar image F1, which two-dimensionally represents a subject's slice section, in real time with a main scan. Herein, the image construction unit 61 constructs the first planar image F1 in real time with acquisition of projection data based on which the first planar image F1 is constructed. In addition to the first planar image F1 constructed in real time, the image construction unit 61 can construct a plurality of kinds of images so that the images will represent part of the subject's slice plane represented by the first planar image F1. A kind of image which the image selection unit 71 selects based on operation data entered at the input unit 31 is constructed. According to the present embodiment, as described later, the image construction unit 61 constructs the first planar image F1 in real time, and constructs at least one of a second planar image F1, a first stereoscopic image S1, a second stereoscopic image S2, a third stereoscopic image S3, a fourth stereoscopic image S4, a fifth stereoscopic image S5, a sixth stereoscopic image S6, and a seventh stereoscopic image S7 according to a selection made by the image selection unit 71. The image construction unit 61 transfers the image data to both the display unit 32 and storage device 33.

The components of the image construction unit 61 will be sequentially described below.

Based on projection data, the planar image construction block 100 reconstructs a two-dimensional planar image F representing a subject's slice plane.

As shown in FIG. 5, the planar image construction block 100 comprises a first planar image construction block 101 and a second planar image construction block 102.

The first planar image construction block 101 included in the planar image construction block 100 reconstructs the two-dimensional first planar image F1 on the basis of projection data. According to the present embodiment, the first planar image construction block 101 constructs the first planar image F1, which represents a subject's slice plane, on the basis of first projection data, which results from a main scan, in real time with execution of the main scan. For example, based on the first projection data resulting from the main scan, the first planar image construction block 101 constructs the first planar images F1, which represent a plurality of subject's axial planes, in real time so that the first planar images will represent different positions in a subject's scan field. The first planar image construction block 101 transfers data items of the first planar images F1 to both the display unit 32 and storage device 33. The first planar images F1 constructed by the first planar image construction block 101 are displayed on the display unit 32 in real time with execution of the main scan.

The second planar image construction block 102 included in the planar image construction block 100 reconstructs a second planar image F2, which represents a subject's axial plane, on the basis of second projection data resulting from a preliminary scan. When the image selection unit 71 selects the second planar image, the second planar image construction block 102 constructs the second planar image F2, and transmits the constructed second planar image F2 to the display unit 32 and storage device 33. The second planar image F2 constructed by the second planar image construction block 102 is displayed on the screen of the display unit in real time with execution of the main scan so that it will be juxtaposed with the first planar images F1 which are constructed by the first planar image construction block 101 and which are displayed on the display unit 32.

The stereoscopic image construction block 200 reconstructs a stereoscopic image S, which three-dimensionally represents a subject's slice plane, on the basis of projection data. The stereoscopic image construction block 200 constructs a stereoscopic image S, which represents a subject's slice plane, according to a volume rendering technique or a surface rendering technique.

As shown in FIG. 5, the stereoscopic image construction block 200 comprises a first stereoscopic image construction block 201, a second stereoscopic image construction block 202, a third stereoscopic image construction block 203, a fourth stereoscopic image construction block 204, a fifth stereoscopic image construction block 205, a sixth stereoscopic image construction block 206, and a seventh stereoscopic image construction block 207. The stereoscopic image construction block 200 is designed to be able to construct a plurality of kinds of stereoscopic images S. The stereoscopic image construction block 200 constructs a kind of stereoscopic image S selected by the image selection unit 71 according to operation data entered at the input unit 31. Specifically, as described later, the stereoscopic image construction block 200 constructs as stereoscopic images S a first stereoscopic image S1, a second stereoscopic image S2, a third stereoscopic image S3, a fourth stereoscopic image S4, a fifth stereoscopic image S5, a sixth stereoscopic image S6, and a seventh stereoscopic image S7. Namely, the stereoscopic image construction block 200 constructs stereoscopic images S that represent a plurality of slice planes including an axial plane, a sagittal plane, a coronal plane, and an oblique plane. The stereoscopic images S constructed by the stereoscopic image construction block 200 are displayed on the screen of the display unit 32 in real time with execution of the main scan so that they will be juxtaposed with the first planar images F1 which are constructed by the first planar image construction block 101 and which are displayed on the display unit 32. Incidentally, the stereoscopic image construction block 200 constructs each of the stereoscopic images S using, for example, images representing a plurality of slice planes. For example, weights to be applied to luminance levels of respective pixels constituting each of the images of slice planes are adjusted proportionally to the distances of the images in a depth direction on a screen, whereby the images are shaded in the depth direction in order to produce a stereoscopic image S. Moreover, a projection image indicating a maximum luminance level, a projection image indicating a minimum luminance level, or a representation indicating a sum total of CT numbers may be adopted.

The first stereoscopic image construction block 201 included in the stereoscopic image construction block 200 reconstructs a three-dimensional first stereoscopic image S1 representing a subject's axial plane. When the image selection unit 71 selects the first stereoscopic image, the first stereoscopic image construction block 201 constructs the first stereoscopic image S1. The first stereoscopic image construction unit 201 then transmits the first stereoscopic image S1 to both the display unit 32 and storage device 33. The first stereoscopic image S1 constructed by the first stereoscopic image construction block 201 is displayed on the screen of the display unit 32 in real time with execution of a main scan so that it will be juxtaposed with the first planar images F1 which are constructed by the first planar image construction block 101 and which are displayed on the display unit 32.

The second stereoscopic image construction block 202 included in the stereoscopic image construction block 200 reconstructs a three-dimensional second stereoscopic image S2, which represents a subject's sagittal plane, on the basis of second projection data resulting from a preliminary scan. Moreover, the second stereoscopic image construction block 202 constructs the second stereoscopic image S2 which represents the subject's sagittal plane, and constructs in association with the second stereoscopic image S2 a slice position image P indicating the positions in a subject's sagittal plane of the subject's axial planes represented by the first planar images F1 constructed by the first planar image construction block 101. When the image selection unit 71 selects the second stereoscopic image, the second stereoscopic image construction block 202 constructs the second stereoscopic image S2 and transmits the second stereoscopic image S2 to both the display unit 32 and storage device 33. The second stereoscopic image S2 and slice position image P constructed by the second stereoscopic image construction block 202 are displayed on the screen of the display unit 32 in association with each other. Specifically, the second stereoscopic image S2 and slice position image P are aligned and then displayed on the screen of the display unit 32 so that they will overlap. Herein, both the second stereoscopic image S2 and slice position image P constructed by the second stereoscopic image construction block 202 are displayed on the screen of the display unit 32 in real time with execution of a main scan so that they will be juxtaposed with the first planar images F1 which are constructed by the first planar image construction block 101 and which are displayed on the display unit 32.

Based on second projection data resulting from a preliminary scan, the third stereoscopic image construction block 203 included in the stereoscopic image construction block 200 constructs a three-dimensional third stereoscopic image S3 representing a subject's oblique plane. When the image selection unit 71 selects the third stereoscopic image, the third stereoscopic image construction block 203 constructs the third stereoscopic image S3, and transmits the third stereoscopic image S3 to both the display unit 32 and storage device 33. The third stereoscopic image S3 constructed by the third stereoscopic image construction block 203 is displayed on the screen of the display unit 32 in real time with execution of a main scan so that it will be juxtaposed with the first planar images F1 which are constructed by the first planar image construction block 101 and which are displayed on the display unit 32.

Based on first projection data resulting from a main scan, the fourth stereoscopic image construction block 204 included in the stereoscopic image construction block 200 constructs a three-dimensional fourth stereoscopic image S4 representing a subject's axial image. When the image selection unit 71 selects the fourth stereoscopic image, the fourth stereoscopic image construction block 204 constructs the fourth stereoscopic image S4 and transmits the fourth stereoscopic image S4 to both the display unit 32 and storage device 33. The fourth stereoscopic image S4 constructed by the fourth stereoscopic image construction block 204 is displayed on the screen of the display unit 32 in real time with execution of a main scan so that it will be juxtaposed with the first planar images F1 which are constructed by the first planar image construction block 101 and which are displayed on the display unit 32.

Based on first projection data resulting from a main scan, the fifth stereoscopic image construction block 205 included in the stereoscopic image construction block 200 constructs a stereoscopic image Sa representing a subject's sagittal plane. Moreover, based on second projection data resulting from a preliminary scan, the fifth stereoscopic image construction block 205 constructs a stereoscopic image Sb representing the subject's sagittal plane. Thereafter, the fifth stereoscopic image construction block 205 overlaps the stereoscopic images Sa and Sb, which represent the sagittal plane, so that images representing a subject's scan field and being contained in the stereoscopic images will be associated with each other, and thus constructs a fifth stereoscopic image F5. When the image selection unit 71 selects the fifth stereoscopic image, the fifth stereoscopic image construction block 205 constructs the fifth stereoscopic image S5 and transmits the fifth stereoscopic image S5 to both the display unit 32 and storage device 33. The fifth stereoscopic image S5 constructed by the fifth stereoscopic image construction block 205 on the basis of the first projection data resulting from the main scan is displayed on the screen of the display unit 32 while being juxtaposed with the first planar images F1. Specifically, the two stereoscopic images S constructed to represent the sagittal plane according to the different projection data items are aligned to overlap, and the fifth stereoscopic image S5 is displayed on the screen of the display unit 23. Incidentally, the fifth stereoscopic image construction block 205 may construct, in addition to the fifth stereoscopic image S5 representing a sagittal plane, the fifth stereoscopic image S5 representing any other plane.

Based on projection data and puncture needle data produced by the puncture needle sensor 51, the sixth stereoscopic image construction block 206 included in the stereoscopic image construction block 200 constructs a sixth stereoscopic image S6 representing a region in which the needlepoint of the puncture needle is located. Specifically, the sixth stereoscopic image construction block 206 constructs as a sixth stereoscopic image S6 an image of a subject's section that covers a region spread in an inserting direction at a predetermined viewing angle with the needlepoint of the puncture needle, which is inserted into the subject, as a point of view. Moreover, for example, the sixth stereoscopic image construction block 206 constructs as the sixth stereoscopic image S6 an image representing a section to which the inserting direction of the puncture needle inserted into the subject is normal. A display image referred to as a so-called virtual endoscopic image is constructed as the sixth stereoscopic image S6. Herein, the sixth stereoscopic image construction block 206 samples an image of a tissue, which is treated using the puncture needle, on the basis of a predetermined threshold, and manipulates the image of the tissue so that the image can be displayed stereoscopically. When the image selection unit 71 selects the sixth stereoscopic image, the sixth stereoscopic image construction block 206 constructs the sixth stereoscopic image S6, and transmits the sixth stereoscopic image to both the display unit 32 and storage device 33. The sixth stereoscopic image S6 constructed by the sixth stereoscopic image construction block 206 is displayed on the screen of the display unit 32 so that it will be juxtaposed with the first planar images F1 which are constructed by the first planar image construction block 101 and which are displayed on the display unit 32.

Based on second projection data resulting from a preliminary scan, the seventh stereoscopic image construction block 207 included in the stereoscopic image construction block 200 constructs a three-dimensional seventh stereoscopic image S7 representing a subject's coronal plane. When the image selection unit 71 selects the seventh stereoscopic image, the seventh stereoscopic image construction block 207 constructs the seventh stereoscopic image S7, and transmits the seventh stereoscopic image to both the display unit 32 and storage device 33. The seventh stereoscopic image S7 constructed by the seventh stereoscopic image construction block 207 is displayed on the screen of the display unit 32 in real time with execution of a main scan so that it will be juxtaposed with the first planar images F1 which are constructed by the first planar image construction block 101 and which are displayed on the display unit 32.

Based on puncture needle data produced by the puncture needle sensor 51, the puncture needle image construction block 301 constructs a puncture needle image N, which virtually represents the puncture needle, in association with the stereoscopic image S constructed by the stereoscopic image construction block 200. For example, the puncture needle image construction block 301 constructs the puncture needle image N so that the position in a subject represented by the puncture needle image will be associated with the position represented by the second stereoscopic image S2 which is constructed by the second stereoscopic image construction block 202 in order to represent a sagittal plane of the subject. Specifically, the puncture needle image construction block 301 constructs the puncture needle image N so that the puncture needle image N constructed to represent the puncture needle will be displayed at a position in the second stereoscopic image S2 which is represented by the puncture needle data. When the image selection unit 71 selects the puncture needle image, the puncture needle image construction block 301 constructs the puncture needle image N, and transmits the puncture needle image N to both the display unit 32 and storage device 33. The puncture needle image N constructed by the puncture needle image construction block 301 is displayed to overlap the second stereoscopic image S2, and displayed on the screen of the display unit 32 in real time with execution of a main scan so that it will be juxtaposed with the first planar images F1 which are constructed by the first planar image construction block 101 and which are displayed on the display unit 32.

Moreover, when an operator enters operation data based on which a kind of stereoscopic image S to be constructed by the image construction unit 61 is selected, the image selection unit 71 included in the central processing device 30 selects a kind of stereoscopic image S, which is constructed by the image construction unit 61, on the basis of the entered operation data. As mentioned above, the image construction unit 61 included in the present embodiment can construct, in addition to the first planar images F1 that are constructed in real time, a plurality of kinds of images representing different slice planes of a subject. The image selection unit 71 selects a kind of image to be constructed by the image construction unit 61 according to operation data entered at the input unit 31. Specifically, the image selection unit 71 selects at least one of the second planar image F2, first stereoscopic image S1, second stereoscopic image S2, third stereoscopic image S3, fourth stereoscopic image S4, fifth stereoscopic image S5, sixth stereoscopic image S6, and seventh stereoscopic image S7, and causes the image construction unit 61 to construct the selected kind of image.

The input unit 31 included in the operator console 3 is an input device including a keyboard and a mouse. The input unit 31 transfers various pieces of information including conditions for scanning and subject information to the central processing device 30 according to an operator's input manipulation. According to the present embodiment, the input unit 31 has an image selection button which an operator uses to enter operation data based on which kind of image to be constructed by the image construction unit 61 is selected. When the operator enters a command, the command is transferred to the image selection unit 71 included in the central processing device 30. For example, when the first stereoscopic image S1 is selected as a kind of stereoscopic image S to be constructed by the stereoscopic image construction block 200 included in the image construction block 61, the input unit 31 transfers a command to the image selection unit 71. Consequently, based on second projection data resulting from a preliminary scan, the first stereoscopic image construction block 201 constructs the first stereoscopic image S1 representing an axial plane of a subject. The first stereoscopic image S1 constructed by the first stereoscopic image construction block 201 is displayed on the display unit 32 in real time with execution of a main scan so that it will be juxtaposed with the first planar images F1 which are constructed by the first planar image construction block 101 and which are displayed on the display unit 32.

The display unit 32 included in the operator console 3 includes, for example, a CRT. An image of a subject's section reconstructed by the image construction unit 61 is displayed on the screen of the display unit 32 according to a command sent from the central processing device 30. On the display unit 32, the planar images F constructed by the first planar image construction block 101 included in the image construction unit 61 are displayed in real time. When the image construction unit 61 constructs a kind of image which the image selection unit 71 selects based on operation data an operator enters at the input unit 31, the image constructed by the image construction unit 61 is displayed on the display unit 32 in real time with execution of a main scan while being juxtaposed with the planar images F constructed by the first planar image construction block 100. According to the present embodiment, the first planar images F1 constructed by the first planar image construction block 101 included in the image construction unit 61 are displayed on the display unit 32 in real time. In addition, at least one of the second planar image F2, first stereoscopic image S1, second stereoscopic image S2, third stereoscopic image S3, fourth stereoscopic image S4, fifth stereoscopic image S5, sixth stereoscopic image S6, and seventh stereoscopic image S7 which the components of the image construction unit 61 construct based on a selection made by the image selection unit 71 is displayed on the display unit 32 while being juxtaposed with the first planar images F1.

Herein, the plurality of first planar images F1 that is constructed by the first planar image construction block 101 and that represents a plurality of subject's axial planes are displayed on the display unit 32 in real time with execution of a main scan. For example, if the first planar image construction block 101 constructs three first planar images F1 representing three axial planes lined in the direction z of the subject's body axis, the three first planar images F1 are displayed on the upper part of the display unit 32 in order of the associated planes lined in the direction z of the subject's body axis.

Assuming that any of the blocks included in the image construction unit 61 constructs at least one of the second planar image F2, first stereoscopic image S1, second stereoscopic image S2, third stereoscopic image S3, fourth stereoscopic image S4, fifth stereoscopic image S5, sixth stereoscopic image S6, and seventh stereoscopic image S7 according to a selection made by the image selection unit 71, the image constructed based on the selection is displayed while being juxtaposed with the first planar images F. For example, as mentioned above, when three first planar images F1 are displayed side by side on the upper part of the screen, the image constructed based on the selection is displayed on the lower part of the screen while being juxtaposed with the first planar images F1.

For example, if the second planar image F2 is selected, data of the second planar image F2 constructed by the second planar image construction block 102 is transferred to the display unit 32. On the screen of the display unit 32, the first planar images F1 are displayed in real time with execution of a main scan, and the second planar image F2 is displayed while being juxtaposed with the first planar images F1.

Likewise, for example, if the first stereoscopic image S1 is selected, data of the first stereoscopic image S1 constructed by the first stereoscopic image construction block 201 is transferred to the display unit 32. On the screen of the display unit 32, the first stereoscopic image S1 is displayed while being juxtaposed with the first planar images F1.

For example, if the second stereoscopic image S2 is selected, data of the second stereoscopic image S2 constructed by the second stereoscopic image construction block 202 is transferred to the display unit 32. According to the present embodiment, the second stereoscopic image construction block 202 constructs, in addition to the second stereoscopic image S2, a slice position image P that indicates the positions in a subject's sagittal plane of the axial planes represented by the first planar images F1. Data of the slice position image P is also transferred to the display unit 32. On the screen of the display unit 32, the first planar images F1 are displayed in real time with execution of a main scan, and the second stereoscopic image S2 and slice position image P are displayed in association with each other so that they will be juxtaposed with the first planar images F1. Specifically, the second stereoscopic image S2 and slice position image P are aligned to overlap and displayed on the screen of the display unit 32.

Likewise, for example, if the third stereoscopic image S3 is selected, data of the third stereoscopic image S3 constructed by the third stereoscopic image construction block 203 is transferred to the display unit 32. On the screen of the display unit 32, the third stereoscopic image S3 is displayed to be juxtaposed with the first planar images F1.

Likewise, for example, if the fourth stereoscopic image S4 is selected, data of the fourth stereoscopic image S4 constructed by the fourth stereoscopic image construction block 204 is transferred to the display unit 32. On the screen of the display unit 32, the fourth stereoscopic image S4 is displayed to be juxtaposed with the first planar images F1.

Likewise, for example, if the fifth stereoscopic image S5 is selected, data of the fifth stereoscopic image S5 constructed by the fifth stereoscopic image construction block 205 is transferred to the display unit 32. On the screen of the display unit 32, the fifth stereoscopic image S5 is displayed to be juxtaposed with the first planar image F1.

Likewise, for example, if the sixth stereoscopic image S6 is selected, data of the sixth stereoscopic image S6 constructed by the sixth stereoscopic image construction block 206 is transferred to the display unit 32. On the screen of the display unit 32, the fifth stereoscopic image S5 is displayed to be juxtaposed with the first planar images F1.

Likewise, for example, if the seventh stereoscopic image S7 is selected, data of the seventh stereoscopic image constructed by the seventh stereoscopic image construction block 207 is transferred to the display unit 32. On the screen of the display unit 32, the seventh stereoscopic image S7 is displayed to be juxtaposed with the first planar images F1.

Moreover, if the puncture needle image construction block 301 constructs the puncture needle image N according to a command an operator enters at the input unit 31, the stereoscopic image S and puncture needle image N are displayed on the display screen 32 in association with each other. For example, the puncture needle image N constructed by the puncture needle image construction block 301 is aligned to match the position of the second stereoscopic image S2 constructed in order to represent a subject's sagittal plane by the second stereoscopic image construction block 202, and displayed on the display unit 32. Namely, on the display unit 32, the puncture needle image N is displayed to overlap the second stereoscopic image S2 representing the subject's sagittal plane. Thus, an image of a puncture needle inserted into a subject during fluoroscopy is virtually displayed to overlap a stereoscopic image of a subject's section.

The storage device 33 included in the operator console 3 is realized with a memory. Various kinds of data including data of subject's images reconstructed by the image construction unit 61 and programs are stored in the storage device 33. The storage device 33 is accessed by the central processing device 30 whenever stored data is needed.

The subject transport unit 4 will be described below.

The subject transport unit 4 carries a subject between the inside of the radiographic space 29 and the outside thereof. The subject transport unit 4 includes a table that has a placement surface on which the subject lies down and which bears the subject. The subject lies, for example, on his/her back on the table and is thus borne by the table. The subject transport unit 4 uses a table mover (not shown) to move the table in a horizontal direction H corresponding to the direction z of the body axis of the subject lying down on the placement surface and a vertical direction V perpendicular to the horizontal surface, and thus carries the subject to the inside of the radiographic space 29. The subject transport unit 4 moves the table within the radiographic space 9 according to the conditions for scanning so as to shift the position of a subject's scan field to be scanned.

The X-ray CT system 1 in accordance with the present embodiment is equivalent to a radiography system in accordance with the present invention. The scanner gantry 2 included in the present embodiment is equivalent to a scanner included in the present invention. Moreover, the input unit 31 included in the present embodiment is equivalent to an input unit included in the present invention. The display unit 32 included in the present embodiment is equivalent to a display unit included in the present invention. The puncture needle sensor 51 included in the present embodiment is equivalent to a treatment instrument sensor included in the present invention. The image construction unit 61 included in the present embodiment is equivalent to an image construction unit included in the present invention. The first planar image F handled in the present embodiment is equivalent to a first image handled in the present invention. The stereoscopic image S handled in the present embodiment is equivalent to a second image handled in the present invention. The stereoscopic image Sa constructed by the fifth stereoscopic image construction block 205 included in the present embodiment is equivalent to a third image handled in the present invention. The slice position image P handled in the present embodiment is equivalent to a slice position image handled in the present invention. The puncture needle image N handled in the present embodiment is equivalent to a treatment instrument image handled in the present invention. The main scan performed in the present embodiment is equivalent to a main scan performed in the present invention. Moreover, the preliminary scan performed in the present embodiment is equivalent to a preliminary scan performed in the present invention.

An example of actions to be performed in order to radiograph a subject using the X-ray CT system 1 in accordance with the present embodiment will be described below.

Figure 6:
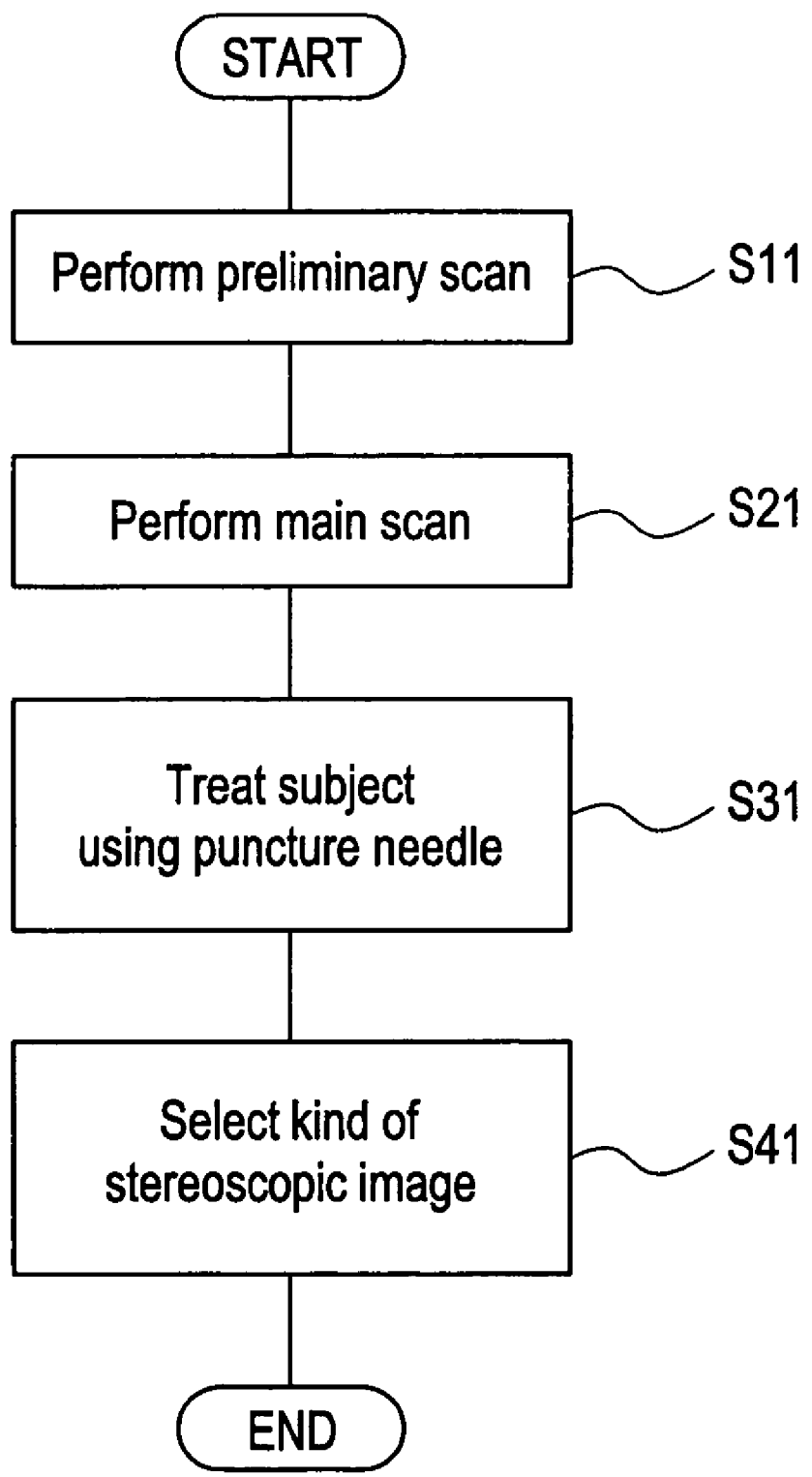
FIG. 6 is a flowchart describing actions to be performed to conduct fluoroscopy using a puncture needle in combination with the X-ray CT system in accordance with the embodiment of the present invention.

FIG. 6 is a flowchart describing actions to be performed in order to achieve fluoroscopy using a puncture needle in combination with the X-ray CT system 1 in accordance with the present embodiment.

As described in FIG. 6, first, a preliminary scan is executed (S11).

Prior to a main scan intended to treat a subject using a puncture needle, a preliminary scan is executed in order to determine the position of a subject's tissue to be treated using the puncture needle during the main scan. For example, the scanner gantry 2 executes the preliminary scan according to an axial scan technique so as to acquire second projection data as projection data. Based on the second projection data resulting from the preliminary scan, the second planar image construction block 102 included in the image construction unit 61 constructs the second planar images F2 representing a plurality of subject's axial planes. An operator uses the second planar images F2 constructed by performing the preliminary scan to determine the position of an object of examination.

Thereafter, the main scan is executed (S21).

Under the conditions for the main scan an operator enters at the input unit 31, the scanner gantry 2 executes the main scan according to the axial scan technique so as to acquire first projection data as projection data. Based on the first projection data resulting from the main scan, the first planar image construction block 101 included in the image construction unit 61 sequentially constructs in real time the first planar images F1 representing a plurality of subject's axial planes so that the first planar images will represent different positions in a subject's scan field. The first planar image construction block 101 transfers data of the constructed first planar images F1 to both the display unit 32 and storage device 33. The first planar images F1 constructed by the first planar image construction block 101 are displayed on the display unit 32 in real time with execution of the main scan.

Thereafter, treatment is performed using a puncture needle (S31).

Herein, an operator references the second planar images F2 constructed to represent axial planes using data resulting from the preliminary scan and the first planar images F1 constructed to represent a plurality of axial planes and displayed in real time with the main scan so as to insert the puncture needle from a predetermined position.

Figure 7A:
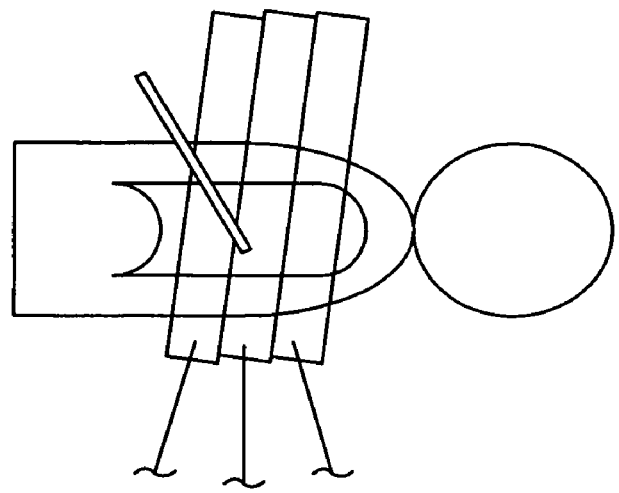
FIG. 7(A) shows the insertion of the puncture needle into the subject by illustrating a subject's sagittal plane.
Figure 7B:
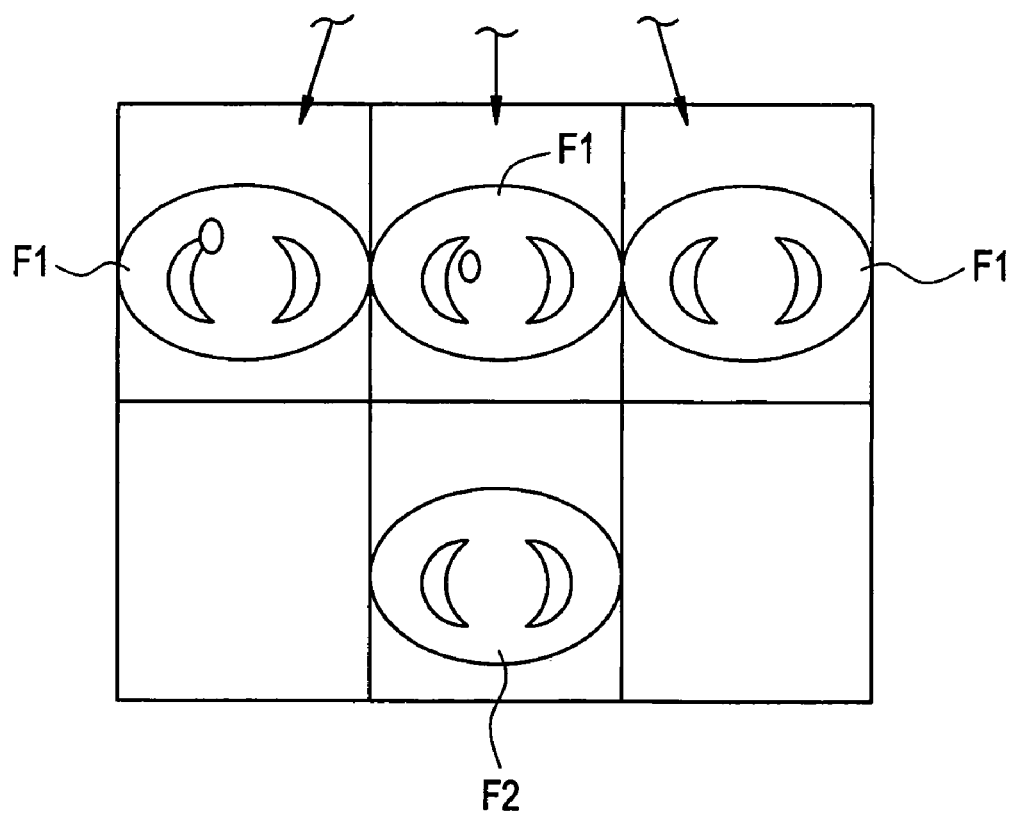
FIG. 7(B) shows screen images displayed on a display unit when the puncture needle is used to perform treatment.

FIG. 7 includes diagrams showing a scene of treatment performed using the puncture needle. FIG. 7(A) shows insertion of the puncture needle into a subject by illustrating a sagittal plane of the subject, and FIG. 7(B) shows screen images displayed on the display unit 32 during the treatment performed using the puncture needle.

For example, assume that the first planar image construction block 101 constructs in real time three first planar images F1 representing three axial planes lined in the direction z of the subject's body axis. In this case, the three first planar images F1 are, as shown in FIG. 7, displayed side by side on the upper part of the screen of the display unit 32 in order of the axial planes lined in the direction z of the subject's body axis. Herein, the second planar images F2 resulting from the preliminary scan are displayed one by one on the lower part of the screen while being juxtaposed with the first planar images F1.

When an operator selects a predetermined kind of stereoscopic image S to be displayed, the selected stereoscopic image S is displayed (S41).

Herein, the operator enters at the input unit 31 operation data based on which kind of stereoscopic image S to be constructed by the image construction unit 61 is selected so that the operator can easily check the location of the puncture needle so as to move the puncture needle to the tissue that is an object of examination. Based on the operation data, the image selection unit 71 selects the kind of stereoscopic image S to be constructed by the image construction unit 61. Herein, the image selection unit 71 selects at least one of the first stereoscopic image S1, second stereoscopic image S2, third stereoscopic image S3, fourth stereoscopic image S4, fifth stereoscopic image S5, sixth stereoscopic image S6, and seventh stereoscopic image S7, and causes the image construction unit 61 to construct the selected kind of image. The image construction unit 61 then transmits the constructed stereoscopic image S to the display unit 32. The stereoscopic image construction block 200 adjusts, for example, weights, which are applied to luminance levels of images representing a plurality of slice planes, proportionally to distances of the images in the depth direction, and thus shades the images in the depth direction so as to construct a stereoscopic image S.

Figure 8:
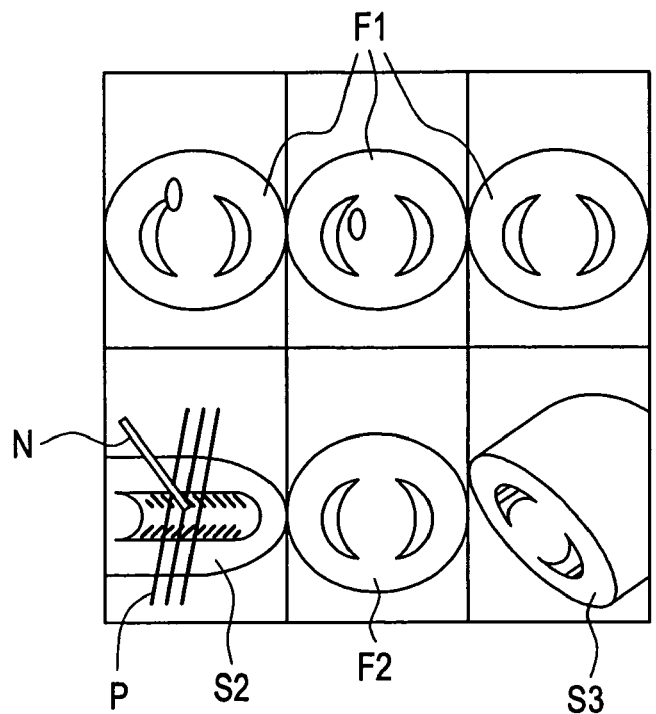
FIG. 8 shows screen images displayed on the display unit in a case where a second stereoscopic image and a third stereoscopic image area selected as stereoscopic images to be handled in the embodiment of the present invention.

FIG. 8 shows screen images displayed on the display unit 32 in a case where the second stereoscopic image S2 and third stereoscopic image S3 are selected as stereoscopic images S.

As shown in FIG. 8, for example, the second stereoscopic image S2 and third stereoscopic image S3 are displayed on the display unit 32 so that they will be juxtaposed with the first planar images F1 and second planar image F2.

Herein, the image selection unit 71 receives from the input unit 31 a notification that an operator has selected the second stereoscopic image S2 and third stereoscopic image S3. The second stereoscopic image construction block 202 included in the image construction unit 61 constructs the second stereoscopic image S2 representing a subject's sagittal plane, and constructs a slice position image P indicating the positions on the subject's sagittal plane of the axial planes represented by the first planar images F1. The third stereoscopic image construction block 203 constructs the third stereoscopic image S3 representing a subject's oblique plane. On the display unit 32, the second stereoscopic image S2 and slice position image P are displayed on the lower part of the screen in association with each other while being juxtaposed with the first planar images F1. Moreover, the third stereoscopic image S3 is displayed on the lower part of the screen while being juxtaposed with the first planar images F1.

If the puncture needle image construction block 301 constructs the puncture needle image N according to a command an operator enters at the input unit 31, the stereoscopic image S and puncture needle image N are displayed on the display unit 32 in association with each other. For example, the puncture needle image N constructed by the puncture needle image construction block 301 is aligned to match the position of the second stereoscopic image S2 which the second stereoscopic image construction block 202 constructs to represent a subject's sagittal plane, and displayed on the display unit 32. Namely, on the display unit 32, the puncture needle image N is displayed to overlap the second stereoscopic image S2 representing the subject's sagittal plane so that the image of the puncture needle being inserted into the subject during fluoroscopy will be virtually displayed to overlap a stereoscopic image of a subject's section.

Figure 9:
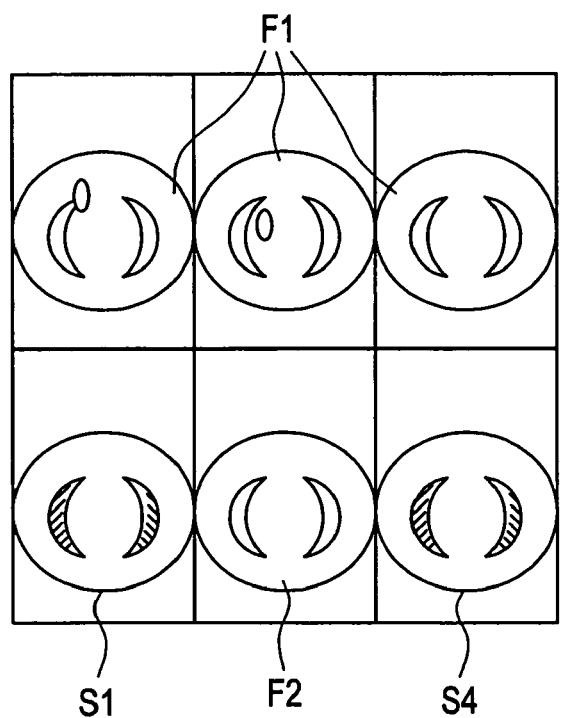
FIG. 9 shows screen images displayed on the display unit in a case where a first stereoscopic image and a fourth stereoscopic image are selected as stereoscopic images to be handled in the embodiment of the present invention.

FIG. 9 shows screen images displayed on the display unit 32 in a case where the first stereoscopic image S1 and fourth stereoscopic image S4 are selected as stereoscopic images S.

As shown in FIG. 9, for example, the first stereoscopic image S1 and fourth stereoscopic image S4 are displayed on the display unit 32 so that they will be juxtaposed with the first planar images F and second planar image F.

In this case, data of the first stereoscopic image S1 which the first stereoscopic image construction block 201 constructs to represent an axial plane using second projection data resulting from a preliminary scan, and data of the fourth stereoscopic image S4 which the fourth stereoscopic image construction block 204 constructs to represent an axial plane using first projection data resulting from a main scan are transferred to the display unit 32. Thereafter, the first stereoscopic image S1 and fourth stereoscopic image S4 are displayed together with the first planar images F and second planar image F on the display unit 32.

Figure 10:
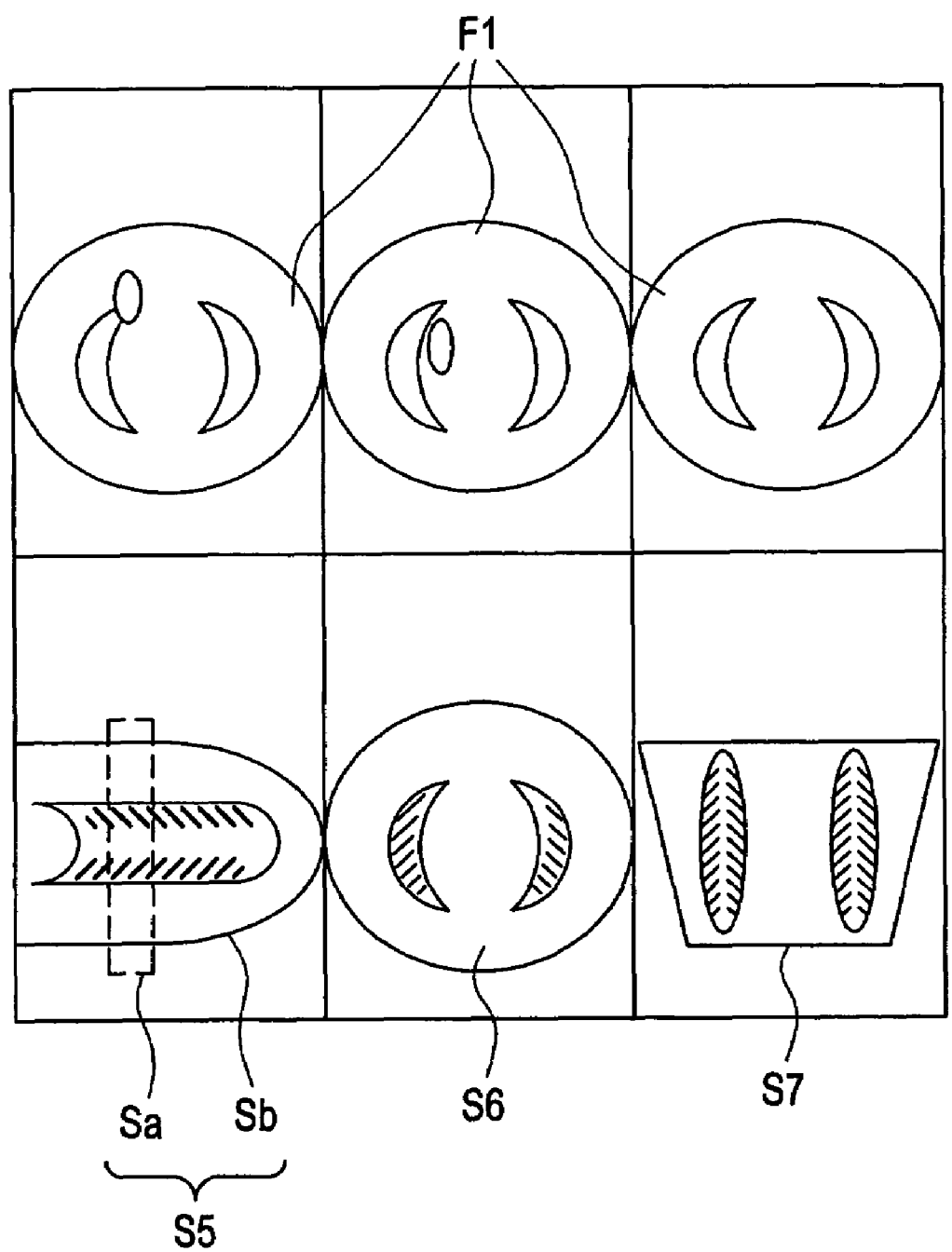
FIG. 10 shows screen images displayed on the display unit in a case where a fifth stereoscopic image, a sixth stereoscopic image, and a seventh stereoscopic image are selected as stereoscopic images to be handled in the embodiment of the present invention.

FIG. 10 shows screen images displayed on the display unit 32 in a case where the fifth stereoscopic image S5, sixth stereoscopic image S6, and seventh stereoscopic image S7 are selected as stereoscopic images S.

As shown in FIG. 10, for example, the fifth stereoscopic image S5, sixth stereoscopic image S6, and seventh stereoscopic image S7 are displayed on the display unit 32 so that they will be juxtaposed with the first planar images F.

In this case, data of the fifth stereoscopic image S5 constructed by the fifth stereoscopic image construction block 205 is transferred to the display unit 32. Moreover, data of the sixth stereoscopic image which the sixth stereoscopic image construction block 206 constructs to represent a region, in which the needlepoint of the puncture needle is located, using the puncture needle data produced by the puncture needle sensor 51 is transferred to the display unit 32. Data of the seventh stereoscopic image S7 constructed by the seventh stereoscopic image construction block 207 is then transferred to the display unit 32. Thereafter, the fifth stereoscopic image S5, sixth stereoscopic image S6, and seventh stereoscopic image S7 are displayed on the display unit 32 so that they will be juxtaposed with the first planar images F1.

An operator checks if the puncture needle has reached the tissue that is an object of examination, and then performs treatment. Thereafter, when the treatment is completed, a scan is executed. The operator checks the treated state and completes fluoroscopy.

As mentioned above, according to the present embodiment, when a subject's tissue is treated using a puncture needle, the first planar image construction block 101 included in the image construction unit 61 reconstructs in real time two-dimensional planar images F1, which represent subject's slice planes, on the basis of projection data. The stereoscopic image construction block 200 included in the image construction unit 61 constructs three-dimensional stereoscopic images S, which represent the subject's slice planes, on the basis of the projection data. The planar images F constructed by the first planar image construction block 101 are displayed in real time on the screen of the display unit 32. The stereoscopic images S constructed by the stereoscopic image construction block 200 are displayed on the screen of the display unit 32 while being juxtaposed with the first planar images F1 constructed by the first planar image construction block 101. Specifically, the scanner gantry 2 executes a main scan, which is intended to acquire first projection data as projection data by scanning a subject's scan field with X-rays, and a preliminary scan that is intended to acquire second projection data as projection data by scanning the subject's scan field with X-rays in preparation for the main scan prior to the main scan. Based on the second projection data resulting from the preliminary scan, the stereoscopic image construction block 200 included in the image construction unit 61 constructs the stereoscopic images S. Based on the first projection data resulting from the main scan, the first planar image construction block 100 included in the image construction unit 61 constructs the planar images F in real time with execution of the main scan. The planar images F constructed by the first planar image construction block 100 and the stereoscopic images S constructed by the stereoscopic image construction block 200 are displayed on the screen of the display unit 32 in real time with execution of the main scan while being juxtaposed with each other. According to the present embodiment, when the puncture needle is inserted, a tissue located in the vicinity of the object of examination can be checked easily. Consequently, the object of examination can be efficiently diagnosed.

Moreover, according to the present embodiment, the stereoscopic image construction block 200 included in the image construction unit 61 is designed to construct a plurality of kinds of stereoscopic images S. When an operator enters operation data based on which kind of stereoscopic image S to be constructed by the stereoscopic image construction block 200 included in the image construction unit 61 is selected, the image selection unit 71 selects the kind of stereoscopic image S, which is constructed by the stereoscopic image construction block 200 included in the image construction unit 61, on the basis of the operation data. The stereoscopic image construction block 200 included in the image construction unit 61 then constructs the kind of stereoscopic image S which the image selection unit 71 has selected according to the operation data entered at the input unit 31. Consequently, according to the present embodiment, since an image permitting an operator to check a tissue located near an object of examination when the operator inserts a puncture needle can be selected, the object of examination can be efficiently diagnosed.

Moreover, according to the present embodiment, the second stereoscopic image construction block 202 included in the image construction unit 61 constructs the second stereoscopic image S2 representing a subject's sagittal plane. In addition, the second stereoscopic image construction block 202 constructs a slice position image P indicating the positions of a plurality of slice planes, that is, axial planes which are represented by first planar images F1 constructed by the first planar image construction block 101. The second stereoscopic image S2 and slice position image P constructed by the second stereoscopic image construction block 202 are displayed on the screen of the display unit 32 in association with each other. Therefore, according to the present embodiment, when a puncture needle is inserted, the position of a slice plane can be easily checked, and a tissue located in the vicinity of an object of examination can be easily checked. Consequently, the object of examination can be efficiently diagnosed.

According to the present embodiment, the puncture needle sensor 51 senses the location of a puncture needle with which a subject is treated, and produces puncture needle data. Based on the puncture needle data produced by the puncture needle sensor 51, the puncture needle image construction block 301 included in the image construction unit 61 constructs the puncture needle image N, which represents the puncture needle, in association with the stereoscopic image S constructed by the stereoscopic image construction block 200. The stereoscopic image S constructed by the stereoscopic image construction block 200 and the puncture needle image N constructed by the puncture needle image construction block 301 are displayed on the display unit 32 so that they will be virtually associated with each other. According to the present embodiment, a position into which the puncture needle is inserted can be easily checked, and a tissue located in the vicinity of an object of examination can be easily checked. Consequently, the object of examination can be efficiently diagnosed.

The form of implementation of the present invention is not limited to the foregoing embodiment. Various variations may be adopted.

For example, in the aforesaid embodiment, X-rays are adopted as a radiation. The present invention is not limited to X-rays. Alternatively, for example, gamma rays or any other radiation may be adopted.

Many widely different embodiments of the invention may be constructed without departing from the spirit and the scope of the present invention. It should be understood that the present invention is not limited to the specific embodiments described in the specification, except as defined in the appended claims.

The invention claimed is:

1. A radiography system comprising:
   a scanner that scans a subject's scan field with a radiation so as to acquire projection data of the subject, wherein the scanner executes a main scan to acquire first projection data as the projection data by scanning the subject's scan field with radiation, and a preliminary scan to acquire second projection data as the projection data by scanning the subject's scan field with radiation in preparation for the main scan prior to execution of the main scan;

an image construction unit that reconstructs in real time a two-dimensional first image of the subject on the basis of the first projection data in real time with execution of the main scan; and a display unit on which the first image constructed by the image construction unit is displayed in real time, wherein:

the image construction unit constructs a three-dimensional second image of the subject on the basis of the second projection data; and the first image and second image are displayed on the screen of the display unit in real time with the execution of the main scan while being juxtaposed to each other.

2. The radiography system according to claim 1, wherein the image construction unit constructs the first images representing a plurality of subject's axial planes so that they will represent different positions in the scan field, and the first images representing the plurality of axial planes are displayed side by side on the display unit.

3. The radiography system according to claim 1, wherein:

the image construction unit constructs the second image of the subject, and constructs a slice position image indicating the positions of subject's slice planes, which are represented by the plurality of first images, in association with the second image; and the second image and slice position image are displayed on the screen of the display unit in association with each other.

4. The radiography system according to claim 1, wherein:

after constructing a three-dimensional third image on the basis of the first projection data, the image construction unit causes the third image to overlap the second image so that the images of the subject's scan field contained in the second and third images will be associated with each other; and the second image which the third image overlaps is displayed on the screen of the display unit while being juxtaposed with the first image.

5. The radiography system according to claim 1, further comprising a treatment instrument sensor that senses the location in the subject of a treatment instrument with which the subject's scan field is treated, and produces treatment instrument data, wherein:

the image construction unit constructs a treatment instrument image, which represents the treatment instrument, on the basis of the treatment instrument data, which is produced by the treatment instrument sensor, in association with the second image; and the second image and treatment instrument image are displayed on the display unit in association with each other.

6. The radiography system according to claim 5, wherein the treatment instrument sensor produces the treatment instrument data concerning the treatment instrument such as a puncture needle, and the image construction unit constructs the second image, which represents a region in which the needlepoint of the puncture needle is located, on the basis of the treatment instrument data produced by the treatment instrument sensor.

7. The radiography system according to claim 5, wherein the treatment instrument sensor produces the treatment instrument data concerning the treatment instrument such as a puncture needle, and the image construction unit constructs the second image, which represents a region in which the needlepoint of the puncture needle is located, on the basis of the treatment instrument data produced by the treatment instrument sensor.

8. The radiography system according to claim 1, further comprising an input unit for use in entering operation data based on which a kind of second image to be constructed by the image construction unit is selected, wherein:

the image construction unit is designed to be able to construct a plurality of kinds of second images; and the image construction unit constructs a kind of second image designated based on the operation data entered at the input unit.

9. A radiography system comprising:

a scanner that scans a subject's scan field with radiation so as to acquire projection data of the subject, wherein the scanner executes a main scan to acquire first projection data as the projection data by scanning the subject's scan field with radiation, and a preliminary scan to acquire second projection data as the projection data by scanning the subject's scan field with radiation in preparation for the main scan prior to execution of the main scan;

an image construction unit that reconstructs in real time a two-dimensional first image of the subject on the basis of the second projection data and constructs a three-dimensional second image on the basis of the first projection data; and a display unit on which the first image and second image are displayed in real time with the execution of the main scan while being juxtaposed to each other.

10. The radiography system according to claim 9, further comprising an input unit for use in entering operation data based on which a kind of second image to be constructed by the image construction unit is selected, wherein:

the image construction unit is designed to be able to construct a plurality of kinds of second images; and the image construction unit constructs a kind of second image designated based on the operation data entered at the input unit.

11. The radiography system according to claim 9, further comprising a treatment instrument sensor that senses the location in the subject of a treatment instrument with which the subject's scan field is treated, and produces treatment instrument data, wherein:

the image construction unit constructs a treatment instrument image, which represents the treatment instrument, on the basis of the treatment instrument data, which is produced by the treatment instrument sensor, in association with the second image; and the second image and treatment instrument image are displayed on the display unit in association with each other.

* * * * *